(12) United States Patent
Mattes et al.

(10) Patent No.: US 12,290,442 B2
(45) Date of Patent: May 6, 2025

(54) MEDICAL PRODUCT AND MEDICAL KIT FOR USE WHEN TREATING A BONE CAVITY, IN PARTICULAR FOR USE WHEN FILLING AND/OR CLOSING A BONE CAVITY

(71) Applicant: Aesculap AG, Tuttlingen (DE)

(72) Inventors: Ursula Mattes, Renquishausen (DE); Michael Utz, Tuttlingen (DE)

(73) Assignee: AESCULAP AG, Tuttlingen (DE)

( * ) Notice: Subject to any disclaimer, the term of this patent is extended or adjusted under 35 U.S.C. 154(b) by 995 days.

(21) Appl. No.: 17/244,850

(22) Filed: Apr. 29, 2021

(65) Prior Publication Data

US 2021/0244541 A1 Aug. 12, 2021

Related U.S. Application Data

(63) Continuation of application No. 16/063,617, filed as application No. PCT/EP2016/081591 on Dec. 16, 2016, now abandoned.

(30) Foreign Application Priority Data

Dec. 18, 2015 (DE) ........................ 10 2015 226063.1

(51) Int. Cl.
*A61F 2/28* (2006.01)
*A61F 2/44* (2006.01)
(Continued)

(52) U.S. Cl.
CPC .................. *A61F 2/28* (2013.01); *A61F 2/44* (2013.01); *A61L 27/04* (2013.01); *A61L 27/045* (2013.01);
(Continued)

(58) Field of Classification Search
CPC .. A61F 2/3872; A61F 2/28; A61F 2002/2835; A61F 2002/4415;
(Continued)

(56) References Cited

U.S. PATENT DOCUMENTS 5,397,359 A 3/1995 Mitteflmeier et al.
5,665,119 A 9/1997 Koller
(Continued)

FOREIGN PATENT DOCUMENTS

DE 102006055432 5/2008
DE 102012213246 1/2014
EP 0366018 5/1990

OTHER PUBLICATIONS

German Search Report dated Oct. 19, 2016, of corresponding German Patent Application No. 10 2015 226 063.1.
(Continued)

*Primary Examiner* — Marcia L Watkins
(74) *Attorney, Agent, or Firm* — Lewis Kohn & Walker LLP; David M. Kohn

(57) ABSTRACT

A medical product, preferably for use in treating, in particular filling and/or closing a bone cavity, wherein the product comprises a plurality of interconnected members, wherein each member has a peripheral boundary and the boundaries of adjacent members engage with one another. And a method for producing a medical product, preferably for use in treating, in particular filling and/or closing a bone cavity, wherein the product comprises a plurality of interconnected members, wherein each member has a peripheral boundary and the boundaries of adjacent members engage with one another.

23 Claims, 7 Drawing Sheets

(51) Int. Cl.

| | |
|---|---|
| *A61L 27/04* | (2006.01) |
| *A61L 27/06* | (2006.01) |
| *A61L 27/10* | (2006.01) |
| *A61L 27/14* | (2006.01) |
| *A61L 27/16* | (2006.01) |
| *A61L 27/18* | (2006.01) |
| *A61L 27/20* | (2006.01) |
| *A61L 27/50* | (2006.01) |
| *A61L 27/54* | (2006.01) |
| *A61F 2/30* | (2006.01) |

(52) U.S. Cl.
CPC ............... *A61L 27/06* (2013.01); *A61L 27/10* (2013.01); *A61L 27/14* (2013.01); *A61L 27/16* (2013.01); *A61L 27/18* (2013.01); *A61L 27/20* (2013.01); *A61L 27/50* (2013.01); *A61L 27/54* (2013.01); *A61F 2002/2835* (2013.01); *A61F 2002/2839* (2013.01); *A61F 2002/30062* (2013.01); *A61F 2002/30113* (2013.01); *A61F 2002/30115* (2013.01); *A61F 2002/30138* (2013.01); *A61F 2002/30171* (2013.01); *A61F 2002/302* (2013.01); *A61F 2002/30588* (2013.01); *A61F 2002/30909* (2013.01); *A61F 2002/3092* (2013.01); *A61F 2002/4415* (2013.01); *A61F 2002/4495* (2013.01); *A61L 2300/258* (2013.01); *A61L 2300/404* (2013.01); *A61L 2300/406* (2013.01); *A61L 2300/41* (2013.01); *A61L 2300/414* (2013.01); *A61L 2300/42* (2013.01); *A61L 2430/02* (2013.01)

(58) Field of Classification Search
CPC ........... A61F 2002/30973; A61L 27/04; A61L 27/10; A61L 27/14; A61L 27/365
See application file for complete search history.

(56) References Cited

U.S. PATENT DOCUMENTS

| | | | |
|---|---|---|---|
| 10,596,660 | B2 | 3/2020 | McCarthy et al. |
| 2003/0055511 | A1 | 3/2003 | Schryver et al. |
| 2006/0041262 | A1 | 2/2006 | Calvert et al. |
| 2007/0260313 | A1 | 11/2007 | Sidler |
| 2011/0125256 | A1 | 5/2011 | Reichenbach et al. |
| 2011/0288653 | A1 | 11/2011 | Sidler |
| 2012/0232654 | A1 | 9/2012 | Sharp et al. |
| 2012/0321878 | A1 | 12/2012 | Landon et al. |
| 2013/0158672 | A1 | 6/2013 | Hunt |
| 2014/0037873 | A1 | 2/2014 | Cheung et al. |
| 2017/0165790 | A1 | 6/2017 | McCarthy |

OTHER PUBLICATIONS

International Search Report dated Mar. 23, 2017, of corresponding International Patent Application No. PCT/EP2016/081591.

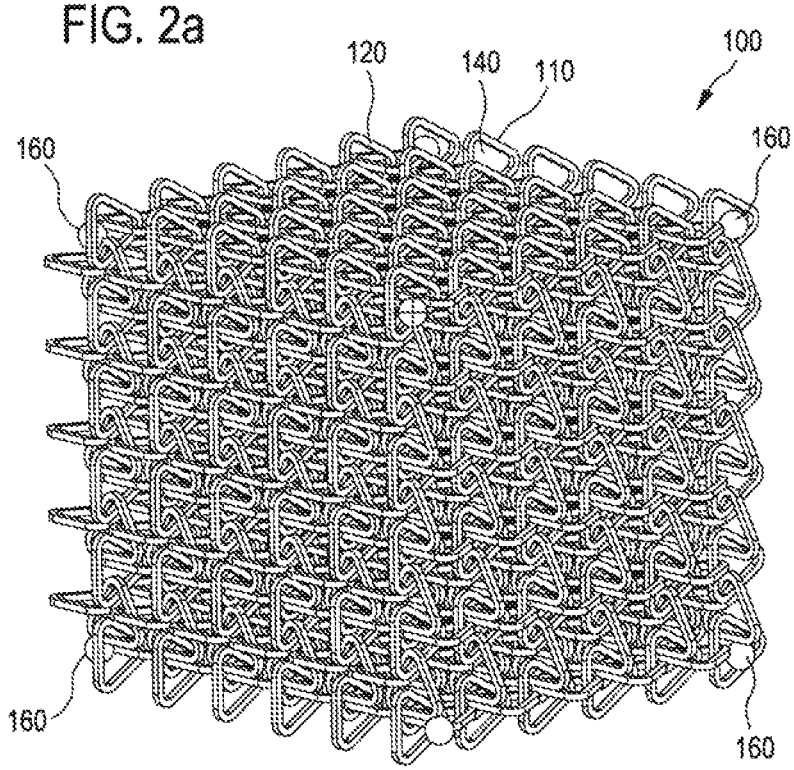

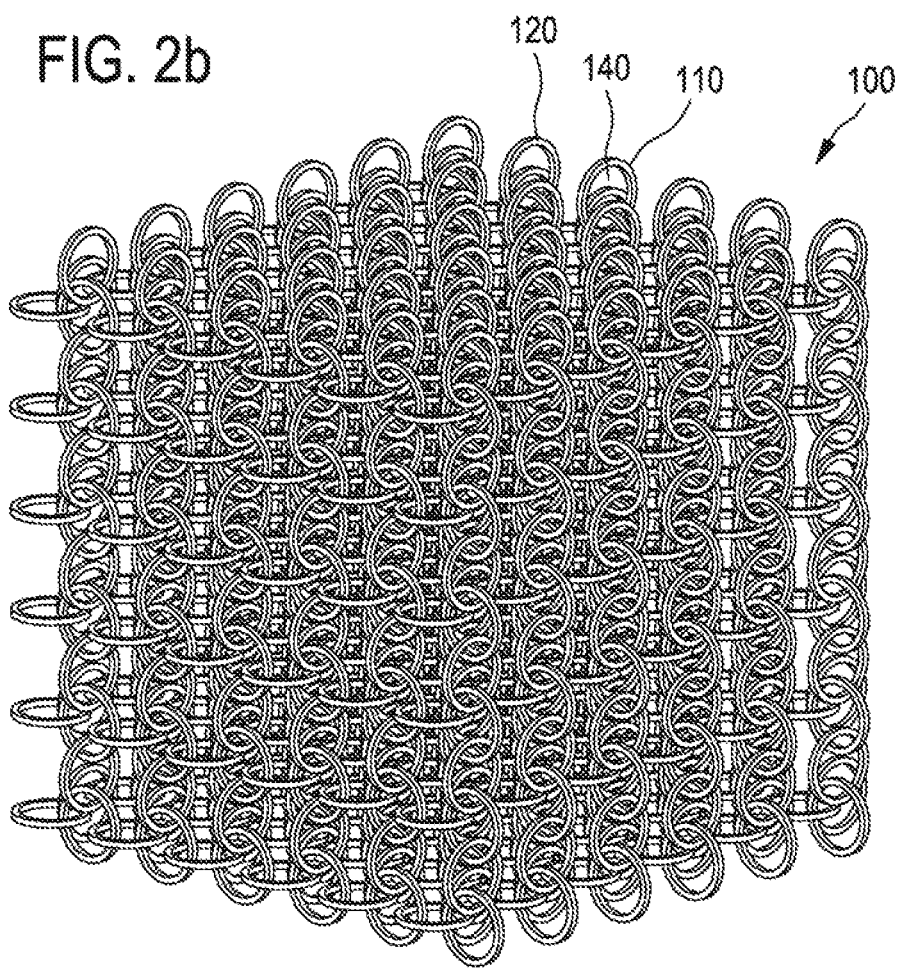

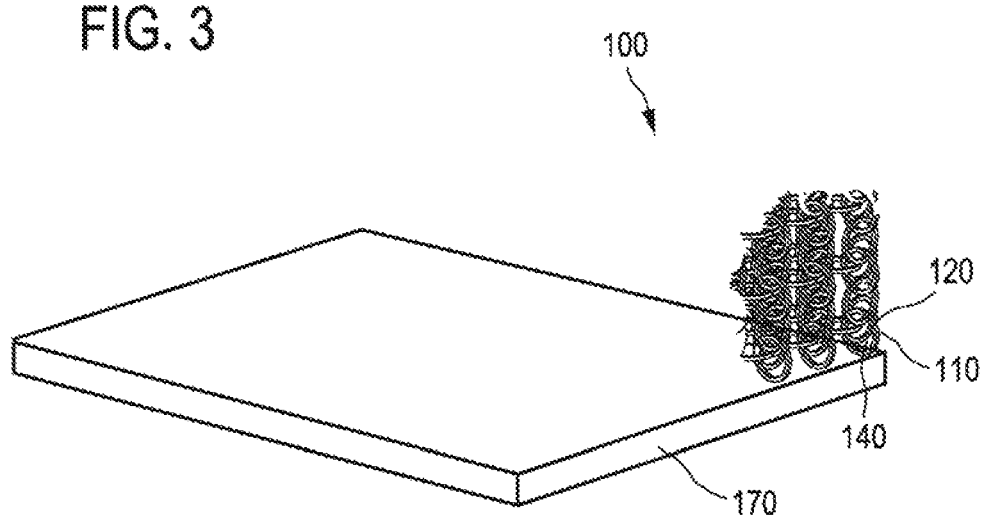

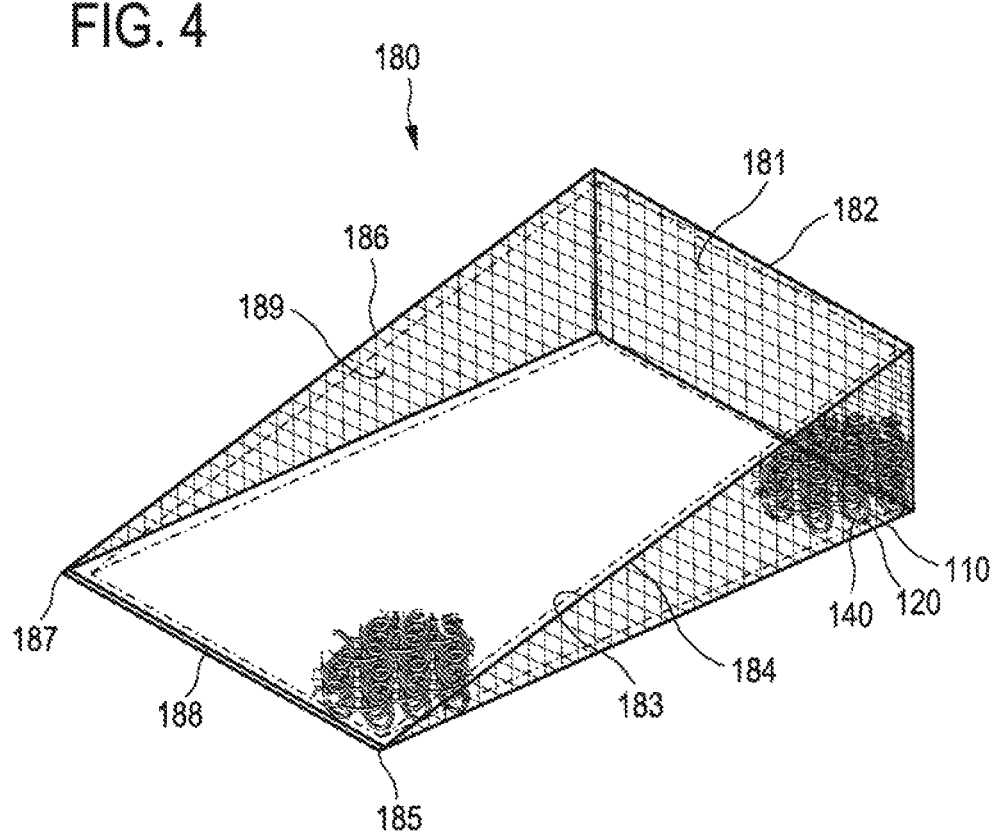

MEDICAL PRODUCT AND MEDICAL KIT FOR USE WHEN TREATING A BONE CAVITY, IN PARTICULAR FOR USE WHEN FILLING AND/OR CLOSING A BONE CAVITY

FIELD OF APPLICATION AND PRIOR ART

The invention relates to a medical product and a medical kit, both of which are preferably provided for use in treating, in particular filling and/or closing a bone cavity.

Particularly in the case of repairs following total hip or knee arthroplasty, it is often necessary to fill cavitary bone defects. In particular, the filling of bone defects is also sometimes necessary in the area of spinal and trauma surgery.

However, filling of cavitary bone defects is often difficult, particularly in the case of bones affected by osteoporosis and tumors.

Several therapeutic options are currently available for intraoperative filling of bone cavities.

One treatment option lies in the use of patent-specific bones. Alternatively, bones from a bone bank can be used. If neither of these options is available, one must use either a metallic bone replacement material or a cement-type bone replacement material, such as e.g. calcium phosphate, hydroxyapatite or the like. As a rule, these materials are in the form of a hard, pressed molded part or a loose powder. Intraoperative adaptation of these solid, artificial bone replacement materials is extremely difficult or even impossible, so that it is often impossible to completely fill bone cavities, with the result that hollow spaces remain in the cavities.

A further drawback is that generic bone replacement materials can often only be implanted in bone cavities with small access openings to an insufficient degree. On the one hand, powdered bone replacement materials can be more favorably placed in such cavities. However, powdered bone replacement materials are disadvantageous in that they have only limited load-bearing properties.

OBJECTIVE AND MEANS FOR ACHIEVING OBJECTIVE

The object of the present invention is therefore to provide a medical product and a medical kit based thereon that in particular are both suitable for the treatment of bone cavities and avoid to the extent possible the drawbacks of the bone replacement implants and materials known from the prior art.

Moreover, the object of the invention is also to provide a method for producing the medical product and a method for filling a bone cavity.

These objects are achieved by means of a medical product wherein the product comprises a plurality of interconnected members, wherein each member has a peripheral boundary and the boundaries of adjacent members interlock, wherein the product comprises a three-dimensional structure composed of the members, wherein the three-dimensional structure further comprises a multilayer construction, wherein each layer has interconnected members, wherein the respective boundaries of members engage with adjacent layers, a method for producing a medical product, wherein the product comprises a plurality of interconnected members, wherein each member has a peripheral boundary and the boundaries of adjacent members interlock, wherein the product comprises a three-dimensional structure composed of the members, wherein the three-dimensional structure further comprises a multilayer construction, wherein each layer has interconnected members, wherein the respective boundaries of members engage with adjacent layers, wherein a plurality of members is produced with a peripheral boundary by means of an additive or generative production method and interconnected such that the boundaries of the connected members engage with one another, and a medical kit for filling and/or closing a bone cavity, comprising a medical product wherein the product comprises a plurality of interconnected members, wherein each member has a peripheral boundary and the boundaries of adjacent members interlock, wherein the product comprises a three-dimensional structure composed of the members, wherein the three-dimensional structure further comprises a multilayer construction, wherein each layer has interconnected members, wherein the respective boundaries of members engage with adjacent layers and a securing element for securing the product to/in a bone cavity or to/in an implant, and the treatment method disclosed in the description. Preferred embodiments are specified in the dependent claims. The wording of all the claims is hereby expressly incorporated into the content of the present description by reference.

According to a first aspect, the invention relates to a medical product, preferably for use in treating, in particular filling and/or closing a human or animal bone cavity.

The medical product comprises a plurality of interlocking members. Preferably, the members are interconnected without joints or securing means such as e.g. sleeves. Each member has a peripheral boundary, wherein the boundaries of adjacent members interlock or engage with one another or are fitted into one another. The connected members are preferably moveable relative to one another, in particular moveable relative to one another to a limited extent. Preferably, the respective boundaries of the respective connected members engage with one another in such a way that the connected members are moveable relative to one another, in particular moveable relative to one another to a limited extent.

Each of the members preferably has a through opening or a through hole and/or a through channel that is/are surrounded by the boundary. In other words, the boundary of the members preferably defines a through opening, a through hole, or a through channel.

Within the meaning of the present invention, the term "bone cavity" is to be understood to refer to a hollow space in a human or animal bone, in particular a human or animal joint bone, preferably a hip or knee joint bone, or a vertebra. The hollow space can be the result of bone trauma, bone disease, or surgical intervention/reintervention, in particular repair following a total hip or knee arthroplasty. In particular, the bone cavity may be a closed bone cavity ("contained defect") or an open bone cavity ("non-contained defect").

Within the meaning of the present invention, the term "through opening" or "through hole" is to be understood to refer to an opening or a hole having no spatial interruption. Accordingly, the term "through channel" within the meaning of the present invention is to be understood to refer to a channel having no spatial interruption.

Because of the preferred relative mobility of the members with respect to one another, the medical product can be conveniently implanted in bone cavities. Preferably, because of the mobility of the members, the product literally "flows" into the bone cavities. The individual members can be wedged against one another in the cavities. Preferably, the members form a stable load-bearing structure which, because of the openings or channels in the members, shows preferably osteoinductive porosity.

A further advantage of the medical product is that it provides the possibility of screw fixation. For example, if a bone screw is screwed into a structure formed by the members, the structure acts as an expansion anchor and makes it possible to carry out mechanical fixation, for example using bone plates or medullary pins.

The medical product further provides the advantage of being (essentially) capable of completely, or at least largely filling bone cavities. This applies in particular to bone cavities having an internal undercut. It is therefore unnecessary to adapt the bone cavity to be filled, thus making it possible to keep the volume and in particular the opening of the bone cavities as small as possible.

In an embodiment, the boundaries of adjacent members interlock in such a way that each of them engages with a through opening, a through hole, or a through channel of at least one adjacent member.

In a further embodiment, the medical product comprises at least one linear structure composed of the members, preferably a linear chain structure.

In particular, the medical product can be a linear structure composed of the members, preferably a linear chain structure.

In a further embodiment, the members form a plurality of interconnected chains, wherein the boundaries of members of adjacent chains interlock or engage with one another or are fitted into one another. Preferably, the members form a plurality of interconnected chains, wherein the respective boundaries of the members engage with a through opening, a through hole, or a through channel of members of adjacent chains.

In a further embodiment, the medical product comprises a plurality of members, with each of the boundaries of said members engaging with the boundary of at least three further members, in particular at least four further members. Preferably, the medical product comprises a plurality of members, with each of the boundaries thereof engaging with a through opening, a through hole, or a through channel of at least three further members, in particular at least four further members.

In a further embodiment, each of a plurality of inner members is connected to a plurality of further members respectively, wherein the medical product is externally bounded by a number of areas, each having interlocking members along its surface.

In a further embodiment, the medical product has at least one two-dimensional structure composed of the members, in particular in the form of at least one layer or at least one sheet.

Within the meaning of the present invention, the term "two-dimensional structure" is to be understood to refer to a structure that has a significantly larger size in two of its dimensions, preferably its length and width, than in its third dimension, preferably its height or thickness.

In particular, the medical product can be a two-dimensional structure composed of the members.

The two-dimensional structure mentioned in the three preceding paragraphs is preferably a two-dimensional chain structure.

In a further embodiment, the medical product comprises a three-dimensional structure composed of the members.

Preferably, the medical product is a three-dimensional structure composed of the members. In other words, the medical product is preferably in the form of a three-dimensional structure composed of the members. The three-dimensional structure can further comprise a multilayer or multisheet construction, wherein each layer or sheet has interconnected members, wherein the respective boundaries of members engage with adjacent layers or sheets.

The three-dimensional structure mentioned in the two preceding paragraphs is preferably a three-dimensional chain structure.

In a further embodiment, the medical product, in particular a structure composed of the members, is deformable to a limited extent.

In a further embodiment, the medical product, in particular a structure composed of the members, is reversibly deformable.

In a further embodiment, the medical product, in particular a structure composed of the members, is resiliently deformable.

In a further embodiment, the medical product, in particular a structure composed of the members, can be converted into a polyhedral structure. Preferably, the product, in particular a structure composed of the members, can be extended or expanded or unfolded into a polyhedral structure. For example, the polyhedral structure can be a cubical, cuboid, prismatic, pyramidal, or spade-shaped structure or a structure delimited from free-form surfaces.

In an alternative embodiment, the medical product, in particular a structure composed of the members, can be converted into a non-polyhedral structure. Preferably, the product, in particular a structure composed of the members, can be extended or expanded or unfolded into a non-polyhedral structure. For example, the non-polyhedral structure can be a spherical, ellipsoid, toroidal or conical structure.

In a further embodiment, at least some of the members have a closed boundary, i.e. an interruption-free or uninterrupted boundary (boundary without interruptions). According to the invention, it can be provided in particular that the respective boundaries of all members of the medical product are closed.

Within the meaning of the present invention, the term "at least some of the members" can refer to one member, a plurality of members or all of the members of the medical product.

In a further embodiment, each of at least some of the members comprises at least one, in particular only one, opening or interruption, in particular at least one, in particular only one, gap. According to the invention, it can be provided in particular that each of the boundaries of all members of the medical product has at least one, in particular only one, opening or interruption, in particular at least one, in particular only one, gap. In this manner, individual members can be separated from one another, and the medical product can be adapted in shape and size to a bone cavity to be treated.

In a further embodiment, each of at least some of the members has at least one, in particular only one, predetermined breaking point. The predetermined breaking point can for example be configured as a notch, porous structure, perforation or material inclusion. According to the invention, it can be provided in particular that each of the boundaries of all members of the medical product has at least one, in particular only one, predetermined breaking point. In this manner, individual members can be separated from one another, and the medical product, in particular a structure composed of the members, can be reduced in size and better adapted to a bone cavity to be treated.

The members or boundaries can generally be of any desired shape, geometry or external contour, in particular a geometry or shape created, in particular printed, from free-form surfaces.

In particular, the members or boundaries can have a polygonal and/or non-polygonal and/or polyhedral and/or non-polyhedral configuration.

For example, the members or boundaries can have a triangular, quadrangular, pentagonal, hexagonal, heptagonal, octagonal, nonagonal, decagonal, circular, oval-shaped, ellipsoid, ring-shaped, toroidal, cuboid, cubical, prismatic, pyramidal, spade-shaped or star-shaped configuration.

Moreover, the members or boundaries can be differently configured. With respect to possible configurations of the members or boundaries, reference is made in particular to the configurations described in the preceding paragraph.

In a further embodiment, each of the members has an internal diameter (inner diameter) of 0.1 mm to 20 mm, in particular 1.5 mm to 5 mm, preferably 2 mm to 4 mm.

According to a further embodiment, each of the boundaries has a width or thickness (boundary width or thickness) of 0.2 mm to 5 mm, in particular 0.5 mm to 4 mm, preferably 1 mm to 3 mm.

According to a further embodiment, the members of the medical product can be divided into two or more groups, wherein the members of each group are identically configured, and the members of different groups are differently configured.

Preferably, the members of different groups differ in at least one property that is selected from the group comprising or composed of total diameter, inner diameter, size, shape, geometry, external contour, material, boundary width or thickness, color, additives such as active ingredient additives and combinations of two or more of said properties.

According to the invention, it can further be preferred that some members, in particular members in rim and/or edge and/or corner areas of the medical product, have a larger internal diameter than other members of the product, in particular inner members of the product. In this manner, it is also possible in a particularly advantageous manner to secure the product to/in open bone cavities, i.e. so-called "non-contained defects", or to implants.

In a further embodiment, some members, in particular members in rim and/or edge and/or corner areas of the product, have a marking, in particular a colored and/or geometric marking. This can for example make it easier for a user, as a rule a surgeon, to expand or unfold the medical product.

Moreover, it can be preferred according to the invention that some members, in particular members in rim and/or edge and/or corner areas of the medical product, comprise a gripping element. The gripping element can for example have a spherical or cubical configuration. The gripping element facilitates handling for the user in a particularly advantageous manner. The gripping element can further be connected in a monolithic or one-piece manner to the corresponding members. For example, the gripping element can be molded onto the corresponding members. Alternatively, the gripping element can be connected to the corresponding members in a materially locking manner. For example, the gripping element can be glued or welded to the corresponding members.

In a further embodiment, some of the members are interconnected in such a way that they are not moveable relative to one another. This allows a more stable configuration of the medical product, in particular a structure composed of the members, and preferably the corners and/or edges and/or surfaces of such a structure. Preferably, the members in the rim and/or edge and/or corner areas of the product, in particular a structure composed of the members, are interconnected such that they are not moveable relative to one another. The members are preferably interconnected in a materially locking manner, in particular glued and/or welded together. Alternatively, or in combination, the members can have a single-part or single-piece (monolithic) configuration. For example, the members can be produced, in particular printed, by means of an additive or generative production method. With respect to suitable additive or generative production methods, reference is made to the production methods described in the following.

In general, the selection of the material for the members or boundaries provides a further possibility of influencing the properties of the medical product.

With respect to suitable materials for the members or boundaries, there are basically no limitations provided that these materials are biocompatible and thus medically usable or tolerated by patients.

In a further embodiment, the members or boundaries comprise non-resorbable, partially resorbable or resorbable material or are composed of such a material. Reference is made to the following with respect to suitable materials.

In a further embodiment, the members comprise a material or are composed of a material that is selected from the group comprising metals, polymers, ceramic materials, osteoconductive materials, bone cement materials and mixtures or combinations of two or more of said materials.

The metals mentioned in the preceding paragraph are preferably selected from the group composed of stainless steel, magnesium, tantalum, titanium, chromium, cobalt and combinations, in particular alloys, of two or more of the above-mentioned metals. Suitable alloys are for example cobalt-chromium alloys. The use of metals allows the production of durable medical products in a particularly advantageous manner.

The above-mentioned polymers can generally be resorbable, partially resorbable or non-resorbable polymers. The use of resorbable or partially resorbable polymers allows particularly advantageous production of osteoinductive products that promote bone growth in the bone cavities.

Preferably, the polymers are selected from the group composed of polyolefins, polyesters, polyamides, polyhydroxyalkanoates, proteins such as extracellular proteins, polysaccharides such as cellulose derivatives and/or mucopolysaccharides, stereoisomers, in particular diastereomers thereof, salts thereof, copolymers thereof and mixtures of two or more of the above-mentioned polymers.

According to a further embodiment, the polymers can be selected from the group composed of polyolefins, polyethylene (such as low-density polyethylene, highdensity polyethylene and/or ultra-high-molecular-weight-polyethylene (UHMWPE)), polypropylene, polytetrafluorethylene, polyvinylidene chloride, polyvinylidene fluoride, polytetrafluoropropylene, polyhexafluoropropylene, polyacrylate, polymethyl acrylate, polymethylmethacrylate, polyesters, polyethylene terephthalate, polypropylene terephthalate, poly butylene terephthalate, polyamides, polyamide 6, polyamide 6-6, polyamide 6-12, polyamide 12, silk, polylactic acid or polylactide, polyglycolic acid or polyglycolide, poly-3-hydroxy butyrate, poly-4-hydroxy butyrate, polytrimethylene carbonate, poly-8-caprolactone, extracellular proteins, collagen, gelatin, elastin, reticulin, fibronectin, laminin, fibrin, fibrinogen, albumins such as serum albumin, starch, amylose, amylopectin, dextran, dextrin, cellulose, cellulose derivatives such as alkyl cellulose, hydroxyalkyl cellulose, hydroxymethyl cellulose, hydroxyethyl cellulose, hydroxypropyl cellulose, carboxyalkyl cellulose, carboxymethyl cellulose, chitin, chitosan, hyaluronic acid, dextran sulfate, heparin, heparan sulfate, chondroitin sulfate, dermatan sulfate, salts thereof, stereoisomers, in particular diastereomers thereof, copolymers thereof and mixtures of two or more of the above-mentioned polymers.

In a further embodiment, the above-mentioned osteoconductive materials are selected from the group composed of hydroxyapatite, α-tricalcium phosphate, β-tricalcium phosphate and mixtures of at least two of said osteoconductive materials.

In a further embodiment, the above-mentioned bone cement materials comprise a calcium and/or magnesium compound that is selected from the group composed of monocalcium phosphate monohydrate (MCPM), monocalcium phosphate anhydride (MCPA), dicalcium phosphate anhydride (DCPA), dicalcium phosphate dihydrate (DCPD), octacalcium phosphate (OCP), α-tricalcium phosphate (α-TCP), β-tricalcium phosphate (β-TCP), amorphous calcium phosphate (ACP), hydroxyapatite (HA), calcium-deficient hydroxyapatite (CdHA), substituted hydroxyapatite, non-stoichiometric hydroxyapatite, nanoscale hydroxyapatite, tetracalcium phosphate (TTCP), calcium sulfate ($CaSO_4$), calcium sulfate hemihydrate ($CaSO_4 \times 0.5\ H_2O$), calcium sulfate dihydrate ($CaSO_4 \times 2\ H_2O$), calcium oxide (CaO), calcium hydroxide ($Ca(OH)_2$), calcium carbonate ($CaCO_3$), calcium glycerophosphate, calcium citrate, calcium lactate, calcium acetate, calcium tartrate, calcium chloride ($CaCl_2$)), calcium silicate, magnesium hydrogen phosphate ($MgHPO_4$) in the form of hydrates or as anhydrous substance, trimagnesium phosphate ($Mg_3(PO_4)_2$), magnesium dihydrogen phosphate ($Mg(H_2PO_4)_2$) in hydrate form or as an aqueous substance, magnesium chloride ($MgCl_2$) in hydrate form or as anhydrous substance, magnesium glycerophosphate, magnesium hydroxide ($Mg(OH)_2$), magnesium hydroxide carbonate (for example as $4\ MgCO_3 \times Mg(OH)_2 \times 5\ H_2O$), magnesium oxide (MgO), magnesium citrate ($Mg_3(C_6HsO_7)_2$) or $Mg(C_6H_6O_7)$), calcium magnesium carbonate ($CaMg(CO_3)_2$, dolomite and mixtures of two or more of the above-mentioned compounds.

In a further embodiment, the medical product has additional structural elements in addition to the members.

The additional structural elements are preferably arranged between the members of the medical product.

Preferably, the additional structural elements are arranged or integrated inside the medical product.

Particularly preferably, the additional structural elements are located in hollow spaces and/or interstices of the medical product, in particular in hollow spaces and/or interstices of a structure composed of the members.

In particular, hollow spaces and/or interstices of the medical product, in particular hollow spaces and/or interstices of a structure composed of the members, can only be partially occupied by the additional structural elements.

In addition to the members, the additional structural elements provide a further possibility in a particularly advantageous manner of selectively adjusting the properties of the medical product. For example, by means of the additional structural elements, the mechanical stability, stiffness or elasticity, in vivo stability or resorption, flow behavior or osteoconductivity of the medical product can be selectively regulated or controlled.

In a further embodiment, the additional structural elements are configured to be larger than the members. Preferably, the additional structural elements have at least one dimension that is larger than that of the members. In particular, the at least one larger dimension can be the length and/or the thickness or height and/or the diameter, in particular the inner and/or outer diameter, of the additional structural elements.

In a further embodiment, the additional structural elements are configured to be larger than hollow spaces and/or interstices of the medical product, in particular hollow spaces and/or interstices of a structure composed of the members. Preferably, the additional structural elements have at least one dimension that is larger than that of hollow spaces and/or interstices of the medical product, in particular hollow spaces and/or interstices of a structure composed of the members. In particular, the at least one larger dimension can be the length and/or thickness or height and/or the diameter, in particular the inner and/or outer diameter, of the additional structural elements. By means of the embodiments described in this paragraph, stiffening of the medical product can be achieved in a particularly advantageous manner.

In general, the additional structural elements can have any desired shape, geometry or external contour, in particular a geometry or shape created, in particular printed, from free-form surfaces.

In a further embodiment, the additional structural elements are in the form of molded bodies. In other words, according to a further embodiment, the additional structural elements have a regular shape. Within the meaning of the present invention, the term "regular shape" is to be understood in particular to refer to the shapes described in the following.

The additional structural elements, in particular molded bodies, can have a polygonal, in particular a triangular, square, rectangular, pentagonal, hexagonal, heptagonal, octagonal, nonagonal, decagonal or star-shaped cross-section.

In particular, the additional structural elements, in particular molded bodies, can have various cross-sections. With respect to possible cross-sections, reference is made to the cross-sections mentioned in the preceding paragraph.

Moreover, the additional structural elements, in particular molded bodies, can have a polyhedral, in particular a cuboid, cubical, tetrahedral, prismatic, pyramidal, truncated pyramidal or spade-shaped configuration.

Moreover, the additional structural elements, in particular molded bodies, can have various polyhedral configurations. In other words, the additional structural elements, in particular molded bodies, may have various polyhedral shapes. With respect to possible polyhedral configurations, reference is made to the preceding paragraph.

Moreover, the additional structural elements, in particular molded bodies, can have a compress cross-section. For example, the additional structural elements, in particular molded bodies, can have an oval-shaped, in particular circular or elliptical, cross-section.

Moreover, the additional structural elements, in particular molded bodies, can have a non-polyhedral, in particular spherical, conical, truncated conical, ring-shaped, toroidal or circular-cylindrical configuration.

For example, the additional structural elements can have a spherical configuration. In this case, depending on the size of the additional structural elements, various effects can be achieved. For example, if the spherical structural elements are configured to be (significantly) smaller than hollow spaces and/or interstices of the medical product, in particular hollow spaces and/or interstices of a structure composed of the members, the medical product cannot be stabilized, or at best, it can be stabilized only in one direction in space.

Depending on the properties of spherically configured structural elements, however, additional properties can be imparted to the medical product without any (appreciable) effect on "flowability" of the medical product. In contrast, if hollow spaces and/or interstices of the medical product, in particular hollow spaces and/or interstices of a structure composed of the members, are almost completely filled, or if the spherical structural elements are configured to be larger than hollow spaces and/or interstices of the medical product, in particular hollow spaces and/or interstices of a structure composed of the members, for example, a stabilizing/stiffening action can be thus be achieved. If the additional structural elements comprise a resorbable material or if the additional structural elements are composed of such a material, time-dependent stabilizing/stiffening of the medical product can be achieved in a particularly advantageous manner, wherein the stabilizing/stiffening decreases over time.

Moreover, the additional structural elements, in particular molded bodies, can have various non-polyhedral configurations. In other words, the additional structural elements, in particular molded bodies, may be in the form of various non-polyhedrons. Reference is made to the preceding paragraph with respect to possible non-polyhedral configurations.

Moreover, the additional structural elements, in particular molded bodies, can be configured as oligopodes. The oligopodes can be selected from the group composed of tripodes, tetrapodes, pentapodes, hexapodes, heptapodes, octapodes and mixtures of at least two of said oligopodes.

Moreover, the additional structural elements, in particular molded bodies, can be selected from the group composed of polyhedrons, non-polyhedrons, oligopodes and combinations thereof. Reference is made to the preceding paragraphs with respect to possible polyhedron, non-polyhedron and oligopode configurations.

In a further embodiment, the additional structural elements have a star-shaped configuration. In this manner, the interlocking members can be stabilized and slipping of the members with respect to one another can be reduced in a particularly advantageous manner. The "flowability" of the medical product can thus be reduced and its stiffness increased.

In a further embodiment, the additional structural elements have an irregular shape.

In a preferred embodiment, the additional structural elements are not connected to the members. In this embodiment, it can be advantageous if the additional structural elements are configured to be roughly the same size as hollow spaces and/or interstices of the medical product, in particular hollow spaces and/or interstices of a structure composed of the members or are even configured to be larger than hollow spaces and/or interstices of the medical product, in particular hollow spaces and/or interstices of a structure composed of the members. In this way, unintentional release of the additional structural elements from the medical product can be prevented in a particularly advantageous manner.

In a further embodiment, the additional structural elements are connected to the members of the medical product, in particular to at least one part of the members. The connection between the additional structural elements and the members can be based for example on a materially locking connection, in particular a glued and/or welded connection. Alternatively, the additional structural elements and the members can have a one-piece or one-part (monolithic) configuration. In particular, the additional structural elements can be molded onto the members of the medical product. A one-piece configuration or overmolding can be carried out for example by means of an additive or generative production method. With respect to suitable additive or generative production methods, reference is made to the following description in its entirety.

In a further embodiment, the additional structural elements have a longitudinal, in particular rod-shaped, wire-shaped, thread-shaped, or string-shaped configuration. In particular, the additional structural elements can be threads, in particular surgical threads.

In a further embodiment, the additional structural elements are configured as sheetlike structures. The sheetlike structures can be textile sheetlike structures, in particular meshes, or non-textile sheetlike structures, in particular grids and/or plates. Configuration of the additional structural elements as sheetlike structures is advantageous in that stabilizing, in particular stiffening of the medical product is only produced in one direction at best, so that by means of structural elements configured in this manner, the medical product can be selectively equipped with properties without any (appreciable) effect on the "flowability" of the medical product.

In general, the additional structural elements can comprise any desired material or be composed of any desired material, provided that the material is biocompatible and tolerated by the patient. With respect to suitable materials, reference is made to the materials described in connection with the members. The metals, polymers, ceramic materials, osteoconductive materials and bone cement materials described there can thus also be used for the additional structural elements.

Moreover, the additional structural elements can for example comprise a metal or be composed of a metal that is selected from the group composed of stainless steel, magnesium, tantalum, titanium, chromium, cobalt and combinations, in particular alloys, of at least two of said metals.

In a further embodiment, the additional structural elements comprise a resorbable material or are composed of a resorbable material. In particular, use of a resorbable material is advantageous in that stabilizing of the medical product can be configured to be time-dependent. For example, the resorbable material can be selected from the group composed of polyhydroxyalkanoate, polylactic acid or polylactide, polyglycolic acid or polyglycolide, poly-3-hydroxy butyrate, poly-4-hydroxy butyrate, polytrimethylene carbonate, poly-ε-caprolactone, proteins such as extracellular protein, gelatin, collagen, elastin, reticulin, fibronectin, laminin, albumins such as serum albumin, starch, amylose, amylopectin, dextran, cellulose, hydroxymethyl cellulose, carboxymethyl cellulose, chitosan, hyaluronic acid, heparin, heparan sulfate, salts thereof, stereoisomers, in particular diastereomers thereof, copolymers thereof and mixtures of at least two of said materials.

In a further embodiment, the additional structural elements comprise non-resorbable material or are composed of a non-resorbable material. Alternatively, the additional structural elements can comprise a material having long-term stability or be composed of such a material. The use of a non-resorbable material or a material having long-term stability is advantageous in that this at least partially provides the medical product with stability that is (essentially) unlimited in time. For example, the non-resorbable material or material with long-term stability can be selected from the group composed of polyolefin, polyethylene, ultra-high-molecular polyethylene, polypropylene, polytetrafluoroethylene, polyvinylidene chloride, polyvinylidene fluoride, polyacrylate, polymethacrylate, polymethylmethacrylate, polyester, polyethylene terephthalate, polyamide, polyamide 6, polyamide 6-6, polyamide 6-12, silk, stereoisomers, in particular diastereomers thereof, copolymers thereof and mixtures of at least two of said materials.

In a further embodiment, the additional structural elements comprise an osteoconductive material or are composed of an osteoconductive material. Within the meaning of the present invention, the term "osteoconductive material" is to be understood to refer to a material that is configured to promote the ingrowth of bone tissue, in particular new bone tissue, in the medical product and thus integration of the medical product into the bone. The osteoconductive material is preferably selected from the group composed of hydroxyapatite, α-tricalcium phosphate, β-tricalcium phosphate and mixtures of at least two of said osteoconductive materials.

In a further embodiment, the additional structural elements are bone particles, in particular autologous bone particles. In particular, the bone particles can be in the form of bone chips.

In a further embodiment, the members of the medical product are at least partially, in particular completely composed of a resorbable material such as e.g. a polyhydroxyalkanoate, a protein, a polysaccharide or a mixture of at least two of said materials. With respect to possible polyhydroxyalkanoates, proteins and polysaccharides, reference is made to the above description in its entirety.

In a further embodiment, the additional structural elements comprise an elastomeric material or are composed of an elastomeric material. In this way, for example, damping or spring properties of the medical product can be achieved. According to the invention, it is conceivable in particular to configure a medical product provided with elastomeric structural elements reversibly such that it can be compressed for insertion into a bone cavity, and after insertion into the bone cavity, can again be unfolded by removing the force responsible for said compression, making it possible to fill the bone cavity with the medical product. In particular, the elastomeric material can be a silicone and/or a silicone rubber, for example a silicone rubber commercially available under the name SILPURANR.

In a further embodiment, the additional structural elements, in particular at least one part of the additional structural elements, comprise an active ingredient. Preferably, the additional structural elements, in particular at least one part of the additional structural elements, are coated with an active ingredient. Reference is made to the following with respect to examples of a suitable active ingredient.

In a further embodiment, at least one part of the members or boundaries comprises an active ingredient. Preferably, at least one part of the members or boundaries is coated with an active ingredient.

According to the invention, it can be provided in particular that all members of the medical product or all boundaries of the medical product respectively comprise an active ingredient. Preferably, all members of the medical product or all boundaries of the medical product respectively are coated with an active ingredient.

The active ingredient is preferably selected from the group composed of an antimicrobial, in particular an antibiotic active ingredient, a wound-healing-promoting active ingredient, a disinfectant active ingredient, an inflammation-inhibiting or antiinflammatory active ingredient, a procoagulant active ingredient, a growth factor such as bone growth factor (osteoinductive factor), a cell-differentiating factor, a cytoadhesive factor, a cell-recruiting factor, a cell receptor, a cell binding factor, a cytokine, a peptide, a structural protein, an extracellular protein such as collagen, elastin, reticulin and the like, a serum protein such as albumin, polysaccharides such as hyaluronic acid, an oligonucleotide, a polynucleotide, DNA, RNA, salts thereof, stereoisomers, in particular diastereomers, thereof and mixtures of two or more of the above-mentioned active ingredients.

In a particularly preferred embodiment, the active ingredient is a bone growth factor, in particular a bone morphogenetic protein (BMP). The bone morphogenetic protein is preferably selected from the group composed of bone morphogenetic protein 1 (BMP1), bone morphogenetic protein 2 (BMP2), bone morphogenetic protein 3 (BMP3), bone morphogenetic protein 3B (BMP3B), bone morphogenetic protein 4 (BMP4), bone morphogenetic protein 5 (BMP5), bone morphogenetic protein 6 (BMP6), bone morphogenetic protein 7 (BMP7), bone morphogenetic protein 8A (BMP8A), bone morphogenetic protein 8B (BMP8B), bone morphogenetic protein 10 (BMP10), bone morphogenetic protein 15 (BMP15) and mixtures of two or more of the above-mentioned bone morphogenetic proteins.

In a further embodiment, the product, in particular the members or the boundaries, is produced by means of an additive or generative production method. The terms "additive production method" or "generative production method" are to be understood within the meaning of the present invention to refer to methods for the rapid and inexpensive production of models, samples, prototypes, tools, and final products ("additive production"). These methods are often also referred to as rapid prototyping. Production is carried out directly based on computer-internal data models using shapeless (liquids, powder and the like) or shape-neutral (band or wire shaped) material by means of chemical and/or physical processes. An additive or generative production method is advantageous in that it allows members or boundaries to be produced with different dimensions, shapes, geometries, and/or external contours, in particular with different inner and outer diameters. In particular, by means of additive production methods, the size and/or geometric characteristics of individual members within a member chain can be varied and/or combined. Moreover, various sizes and configurations, such as rings, triangles, stars, cubes or the like, can be mixed. Additive or generative production methods thus allow variable production of members in a particular manner, thus making it possible to selectively influence the properties of the medical product. For example, in this manner, it is possible to selectively adapt properties of the medical product, such as e.g. its stiffness, "flowability", mobility and porosity, to the respective bone cavity to be treated. The degree of "interspersing" of individual members can also be particularly conveniently adjusted by means of additive or generative production methods.

The additive or generative production method can be selected from the group composed of powder bed methods, free space methods, and liquid material methods.

The powder bed method can be selected from the group composed of selective laser melting, selective laser sintering, selective heat sintering, solidification of powder material by means of a binder (binder jetting), and electron beam melting.

The free space method can be selected from the group composed of fused deposition modelling, LOM (laminated object modelling) methods, cladding, wax deposition modeling, contour grafting, cold gas spraying, and electron beam melting.

The liquid material method can be selected from the group composed of stereolithography, DLP (digital light processing) methods, and LCM methods. The LCM method can be a liquid composite molding method or a lithography-based ceramic manufacturing method.

In a further embodiment, the medical product further comprises a covering element. Within the meaning of the present invention, the term "covering element" is to be understood to refer to an element that is configured such that it allows a bone cavity to be covered or closed. In this way, the medical product is suitable in a particularly advantageous manner not only for filling a bone cavity, but also for covering or closing a bone cavity filled by the members of the medical product.

The covering element preferably has a planar configuration. In particular, the covering element can have a two-dimensional structure.

The covering element can further comprise a grid structure or be in the form of a grid structure.

The covering element is preferably a covering element with a plate-type configuration, in particular a grid configuration. In particular, the covering element can be in the form of at least one plate, in particular at least one grid plate. Within the meaning of the present invention, the term "at least one plate" defines one plate or a plurality of plates, i.e. two, three, or more plates. This definition also applies mutatis mutandis to the term "at least one grid plate". According to the invention, it is particularly preferable for the covering element to be in the form of a plate, in particular a grid plate.

In a preferred embodiment, at least one part of the members, in particular only one part of the members, is connected to the covering element. In this case, the at least one part of the members can be connected to the covering element in a materially locking manner. For example, the connection between the at least one part of the members and the covering element can be based on an adhesive and/or welded connection. Alternatively, the at least one part of the members and the covering element can have a one-piece or one-part (monolithic) configuration. In particular, the members can be molded onto the covering plate. A one-part configuration or overmolding can be carried out for example by means of an additive or generative production method. With respect to suitable additive or generative production methods, reference is made to the above description in its entirety.

In a further embodiment, the covering element comprises a securing element or a plurality of securing elements. In this way, it is possible to secure the covering element and thus the medical product to surrounding bone tissue. For example, the securing element(s) can be configured in the form of screws, nails, and/or anchors. Alternatively, the covering element can comprise a receiving device, for example in the form of an opening or recess, or a plurality of receiving devices, for example in the form of openings or recesses, for receiving a securing element or a plurality of securing elements.

In a further embodiment, the covering element can be configured in a patent individual or patent-specific manner.

With respect to suitable materials that the covering element can comprise or of which the covering element can be composed, in order to avoid unnecessary repetitions, reference is made to the materials disclosed in the above description with respect to the members, boundaries, and optionally provided additional structural materials in their entirety. The materials thus described can also be used to produce the covering element.

In a further embodiment, the covering element comprises an active ingredient. The covering element can in particular be partially or completely coated with an active ingredient. With respect to examples of a suitable active ingredient, reference is made to the above description.

In a further embodiment, the covering element has load-bearing properties. In this way, the mechanical stability of the product as a whole can be improved.

A medical product with a covering element is suitable in particular for the treatment of tumor-related long bone cavities, in particular tumor-related cavities of the femur and/or humerus.

In a further embodiment, the medical product further comprises an enclosing element (bordering element). Within the meaning of the present invention, the term "enclosing element" ("bordering element") is to be understood to refer to an element that is configured such that it can enclose the members of the medical product.

The enclosing element preferably has load-bearing properties. In this way, greater mechanical stability of the medical product overall can be achieved.

Preferably, the enclosing element has a planar configuration. In particular, the enclosing element can have a two-dimensional structure.

In a further embodiment, the enclosing element comprises a grid structure or is in the form of a grid structure.

In a further embodiment, the enclosing element has a plate-type, in particular a grid plate-type configuration. In particular, the enclosing element can comprise at least one plate, in particular at least one grid plate, or be in the form of at least one plate, in particular at least one grid plate.

In a further embodiment, the enclosing element comprises at least one enclosing part, i.e. one enclosing part (bordering part) or a plurality of enclosing parts (bordering parts). According to the invention, it is preferred if the enclosing element comprises a plurality of enclosing parts, i.e. two or more enclosing parts, in particular three enclosing parts.

In a further embodiment, the enclosing element comprises three enclosing parts, wherein the enclosing parts are a quadrangular, in particular rectangular, enclosing part and two triangular, in particular two non-equilaterally triangular, preferably two right-angled triangular enclosing parts. Preferably, each of the two triangular enclosing parts is connected via its cathetus with opposite sides, preferably opposite narrow sides, of the quadrangular enclosing part. The triangular enclosing parts are preferably arranged parallel or essentially parallel to one another. The free corners of the triangular enclosing parts, i.e. the corners of the triangular enclosing parts that are not included in the connection with the quadrangular enclosing part, preferably point in the same direction. It can be advantageous from the standpoint of stability if the free corners of the triangular enclosing parts are connected via a strut. In the case of non-equilaterally triangular enclosing parts, in particular in the case of right-angled triangular enclosing parts, each of these should be connected with its shorter cathetus to opposite sides, preferably opposite narrow sides, of the quadrangular enclosing part. In this case as well, the triangular enclosing parts are preferably arranged parallel or essentially parallel to one another. In particular, in this case as well, the free corners of the triangular enclosing parts point in the same direction. In this case, each of the free corners is formed by the hypotenuse and the longer cathetus of the triangular enclosing parts. In this case as well, it can be advantageous from the standpoint of stability if the free corners of the triangular enclosing parts are interconnected via a strut.

In a further embodiment, at least one part of the members, in particular only one part of the members, is connected to the enclosing element, in particular to an inner side or optionally a plurality of inner sides of the enclosing element. In this case, the at least one part of the members can be connected to the enclosing element in a materially locking manner, in particular to one or optionally a plurality of inner side(s) of the enclosing element. The materially locking connection can for example be based on an adhesive and/or welded connection. Alternatively, the at least one part of the members and the enclosing element can have a one-piece or one-part (monolithic) configuration. In particular, the members can be molded onto the enclosing element. In particular, one-piece configuration or overmolding can be carried out by means of an additive or generative production method. With respect to suitable additive or generative production methods, reference is made to the above description in its entirety.

In a further embodiment, the enclosing element can be configured in a patient individual or patient-specific manner.

With respect to suitable materials that the enclosing element, in particular the above-mentioned enclosing parts, can comprise or of which the enclosing element, in particular the above-described enclosing parts, can be composed, reference is made to the materials disclosed within the framework of the above description with respect to the members, boundaries, and the optionally provided additional structural elements in their entirety. The materials thus described can also be used for production of the enclosing element, in particular the above-described enclosing parts.

In a further embodiment, the enclosing element comprises a securing element or a plurality of securing elements. In this way, securing of the enclosing element and thus the medical product to the surrounding bone tissue is possible. The securing element(s) can for example be configured in the form of screws, nails, and/or anchors. Alternatively, the enclosing element can comprise a receiving device, for example in the form of an opening or recess, or a plurality of receiving devices, for example in the form of openings or recesses, for receiving a securing element or a plurality of securing elements.

In a further embodiment, the enclosing element comprises an active ingredient. In particular, the enclosing element can be partially or completely coated with an active ingredient. With respect to examples of a suitable active ingredient, reference is made to the above description.

A medical product with an enclosing element is suitable in particular for use in carrying out a total hip arthroplasty, i.e. in carrying out a complete hip replacement.

In a further embodiment, the medical product is a surgical implant, preferably a bone replacement material, in particular for lining bone or joint implants or for use as a counter-bearing for bone or joint implants.

In a further embodiment, the medical product is provided for use in treating, in particular for use in filling and/or closing a bone cavity, in particular a trauma related bone cavity and/or a disease-related, in particular tumor-related bone cavity and/or a bone cavity resulting from surgical intervention/reintervention, in particular a bone cavity resulting from repair after total hip or knee arthroplasty.

The bone cavity mentioned in the above embodiment is preferably an articular bone cavity, long bone cavity and/or vertebral cavity. Particularly preferably, the bone cavity is a hip joint bone cavity, knee joint bone cavity, femoral bone cavity, tibial bone cavity, fibular bone cavity, humeral bone cavity, radial cavity and/or cubital cavity.

According to a second aspect, the invention relates to a method for producing a medical product, in particular for producing a medical product according to the first aspect of the invention.

The method is characterized in particular in that a plurality of members, each having a peripheral boundary, is produced by means of an additive or generative production method and are interconnected such that the respective boundaries of adjacent members interlock or engage with one another or are fitted into one another.

In a preferred embodiment, the boundaries of adjacent members engage with one another in such a way that the connected members are moveable relative to one another, in particular moveable with respect to one another to a limited extent.

In a further embodiment, an additive or generative production method is used that is selected from the group comprising powder bed methods, free space methods and liquid material methods. With respect to further features and advantages of these production methods, reference is made to the methods already described in connection with the first aspect of the invention in their entirety.

Preferably, a 3D printing method is used as an additive or generative production method, in particular selected from the group composed of selective laser melting, electron beam melting, selective laser sintering, stereolithography, digital light processing, polyjet modeling and fused deposition modeling.

In a further embodiment, the members are interconnected in such a way that each of the boundaries of the members engages with a through opening, a through hole, or a through channel of at least one adjacent member, in particular of two, three, or four adjacent members.

In a further embodiment, by means of the additive or generative production method, further gripping elements are configured and connected to some of the members, in particular to members provided for arrangement in rim and/or edge and/or corner areas of the medical product. Preferably, by means of the additive or generative production method, further gripping elements are molded onto some of the members, in particular members provided for arrangement in rim and/or edge and/or corner areas of the medical product.

In a further embodiment, by means of the additive or generative production method, additional structural elements are further configured or produced and arranged or integrated among at least some of the members, in particular in hollow spaces and/or interstices of the medical product, preferably in hollow spaces and/or interstices of a structure composed of the members.

In a further embodiment, by means of the additive or generative production method, additional structural elements are further connected to at least some of the members. Preferably, additional structural elements are further molded onto at least some of the members by means of the additive or generative production method.

In a further embodiment, by means of the additive or generative production method, a covering element is further configured and connected to at least some of the members. Preferably, at least some of the members are further molded onto a covering element by means of the additive or generative production method.

In a further embodiment, by means of the additive or generative production method, an enclosing element (bordering element) is further configured and connected to at least some of the members. Preferably, at least some of the members are fur the molded onto an enclosing element (bordering element) by means of the additive or generative production method.

In a further embodiment, the members or boundaries and/or optionally present gripping elements and/or optionally present additional structural elements and/or an optionally present covering element and/or an optionally present enclosing element is/are further provided, preferably coated, with an active ingredient by means of the additive or generative production method.

With respect to further features and advantages of the method and the medical product, reference is made to the statements with respect to the first aspect of the invention in their entirety.

According to a third aspect, the invention relates to a medical kit, preferably for use in treating, in particular for use in filling and/or closing a bone cavity.

The medical kit comprises a medical product according to the first aspect of the invention and a securing element for securing the product to/in a bone cavity or to/in an implant, preferably a bone implant.

The securing element can in particular be configured such that it allows securing of a covering element and/or enclosing element of the medical product to/in a bone cavity.

For example, the securing element can be one or a plurality of screws, in particular bone screws, one or a plurality of nails, in particular bone nails, and/or one or a plurality of anchors, in particular bone anchors.

With respect to further features and advantages of the kit, in particular the medical product, in order to avoid unnecessary repetitions, reference is made to the statements made with respect to the first aspect of the invention in their entirety. The embodiments and advantages described therein with respect to the medical product also apply to the kit according to the invention.

According to a fourth aspect, the invention relates to a method for treating, in particular filling and/or closing a bone cavity.

The method comprises the following step:
insertion of a medical product according to a first aspect of the invention into the bone cavity.

In a preferred embodiment, the method further comprises the following step:
adaptation of the size of the medical product to the bone cavity, in particular to the size and/or opening of the bone cavity, by means of members with predetermined breaking points. Adaptation of the size of the medical product is preferably carried out before it is inserted into the bone cavity.

In a further embodiment, the method further comprises the following step:
securing of at least one part of the members, in particular only one part of the members, on/in an implant, preferably a bone implant. Preferably, this securing step takes place before the medical product is inserted into the bone cavity.

In a further embodiment, the method further comprises the following step:
pressing of the medical product into the bone cavity, in particular by means of a screw, so that the medical product presses against the walls of the bone cavity.

In a further embodiment, the members of the medical product are clamped and/or wedged into the bone cavity.

In a further embodiment, the method further comprises the following step:
securing of the medical product in the bone cavity, in particular by means of at least one member located in an edge area and/or on a corner. For this purpose, the at least one member in particular can have a larger internal diameter than the other members of the medical product.

In a further embodiment, the method further comprises the following step:
securing of a covering element and/or enclosing element to bone tissue surrounding the bone cavity.

With respect to further features and advantages of the method, in particular the medical product, in order to avoid unnecessary repetitions, reference is made to the statements made concerning the above aspects of the invention, in particularly the first aspect of the invention, in their entirety. The embodiments and advantages described with respect to the medical product also apply to the method according to the invention.

Further advantages and features of the invention can be found in the claims and the following description of preferred exemplary embodiments of the invention, which are presented with reference to the figures.

BRIEF DESCRIPTION OF THE FIGURES

The figures schematically show the following:
FIGS. 2a-c: various embodiments of a product according to the invention,
FIG. 3 a further embodiment of a product according to the invention,
FIG. 4 a further embodiment of a product according to the invention.

MORE DETAILED DESCRIPTION OF THE FIGURES

Figure 1A:
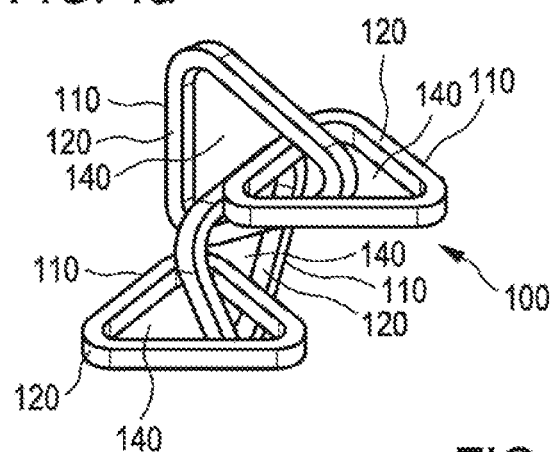
FIGS. 1a-c: sections of various embodiments of a product according to the invention.

FIG. 1a shows a section of a medical product according to the invention 100. The product 100 shows triangular members 110 with a peripheral boundary 120. The corners of the members 110 are preferably rounded off. The respective boundaries 120 are configured to be closed, i.e. without an interruption. Moreover, each of the boundaries 120 defines a through opening 140.

The members 110 are interconnected, wherein the connection is based on interlocking or fitting of the boundaries 120 of adjacent members 110 into one another. Preferably, the boundaries 120 of adjacent members 110 engage with one another in such a way that connected members are moveable with respect to one another to a limited extent.

In the section shown in FIG. 1a, the respective boundaries of the two inner members engage with the boundaries of the immediately adjacent members, while the respective boundaries of the two outer members engage only with the boundary of the immediately adjacent inner member.

Figure 1B:
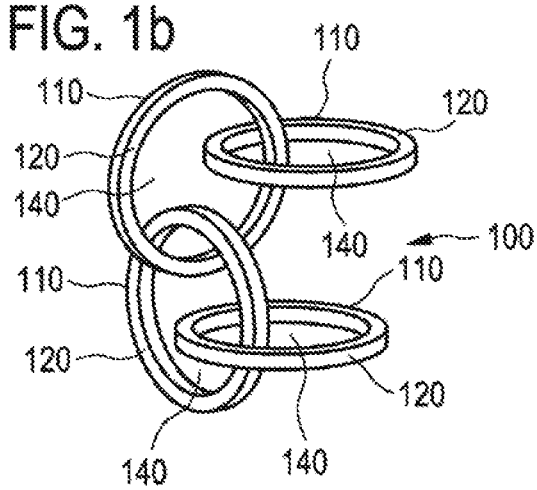

FIG. 1b shows a section of a further product according to the invention 100. The product 100 has ring-shaped members 110 with a peripheral boundary 120. The respective boundaries 120 are configured to be closed, i.e. uninterrupted. Each boundary 120 defines a through opening 140.

Moreover, the statements concerning the product according to the invention 100 shown in FIG. 1a apply mutatis mutandis.

Figure 1C:
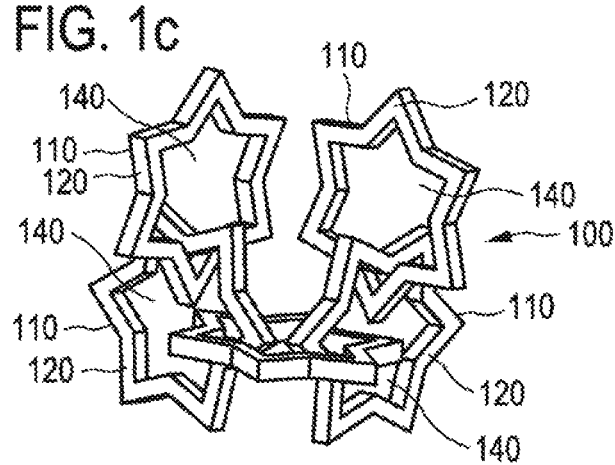

FIG. 1c shows a section of a further product according to the invention 100. The product 100 comprises star-shaped members 110 with a peripheral boundary 120.

The corners of the members 110 preferably have an unrounded configuration. Each of boundaries 120 is configured to be closed, i.e. without an interruption. Each boundary 120 defines a through opening 140.

Moreover, the statements concerning the product according to the invention 100 shown in FIG. 1a apply mutatis mutandis.

In the partial views of a product according to the invention 100 shown in FIGS. 1a through 1c, the interlocking of adjacent boundaries of members results in linking of the members 110.

FIG. 2a shows a further embodiment of a medical product according to the invention 100. The medical product 100 comprises a plurality of members 110. The members 110 are triangular, wherein the corners of the members 110 are preferably rounded. Each member 110 has a peripheral and preferably closed, i.e. uninterrupted, boundary 120. Each of the boundaries 120 encloses an opening 140. The members 110 are interconnected, wherein the connection of the members 110 is based on interlocking or fitting into one another of the boundaries 120 of adjacent members 110. Preferably, the boundaries 120 of adjacent members 110 engage with one another such that the connected members 110 are moveable with respect to one another to a limited extent.

The medical product 100 comprises a plurality of inner members, each of which is connected to a plurality of further members, in particular four further members, wherein the product 100 is bounded on its outside by a number of areas, each having interlocking members along its surface.

The members 110 are moveable with respect to one another to a limited extent. This allows compression of the medical product 100 in a particularly advantageous manner, for example for insertion into bone cavities. Conversely, the limited mobility of the members 110 also allows expansion or unfolding of the product, for example in a cubical structure, as shown in FIG. 2a. The expansion or unfolding of the medical product 100 can be facilitated by gripping or holding elements 160. For example, as shown in FIG. 2a, the gripping or holding elements 160 can have a spherical configuration. Advantageously, the gripping or holding elements 160 are located after expansion or unfolding of the product 100 at the corners of the expanded or unfolded product.

FIG. 2b shows a further embodiment of a medical product according to the invention 100. The medical product 100 comprises a plurality of members 110. The members 110 have an annular configuration. Each member 110 has a peripheral and preferably closed, i.e. uninterrupted, boundary 120. Each of the boundaries 120 encloses an opening 140. The members 110 are interconnected, wherein the connection of the members 110 is based on interlocking or fitting into one another of the boundaries 120 of adjacent members 110. Preferably, the boundaries 120 of adjacent members 110 engage with one another such that the connected members 110 are moveable with respect to one another to a limited extent. Moreover, the statements concerning the product according to the invention 100 shown in FIG. 2a apply mutatis mutandis.

Figure 2C:
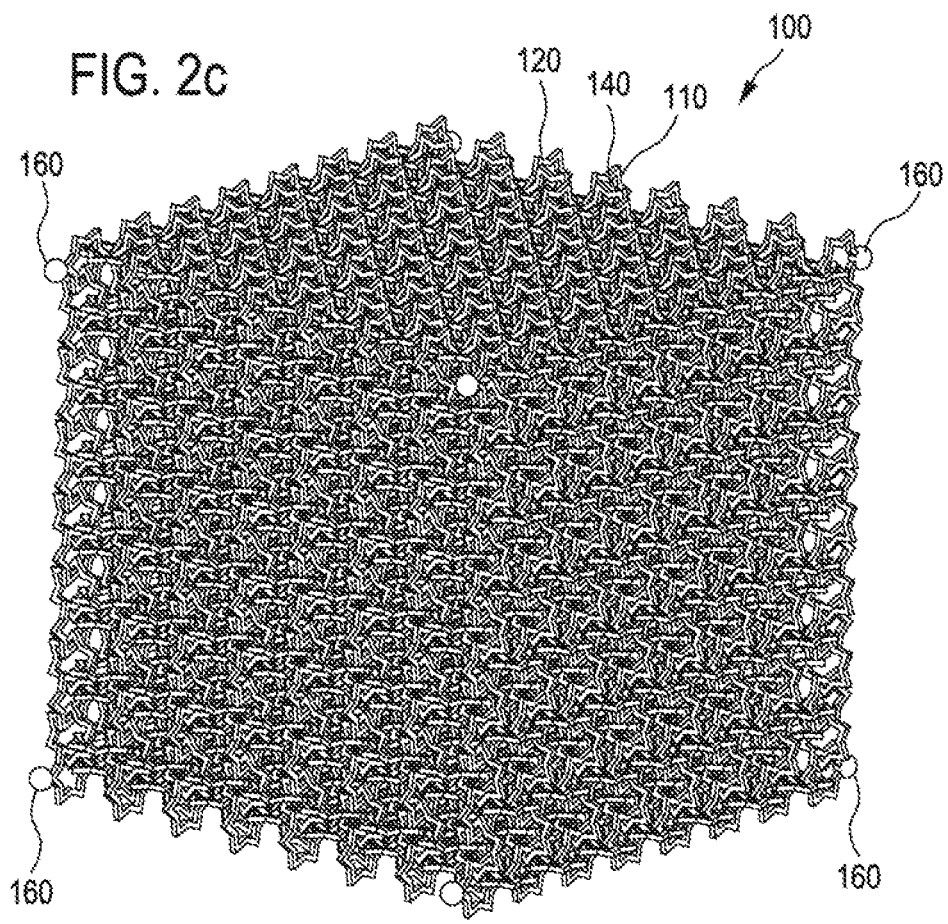

FIG. 2c shows a further embodiment of a medical product according to the invention 100. The medical product 100 comprises a plurality of members 110. The members 110 have a star-shaped configuration. Each member 110 has a peripheral and preferably closed, i.e. uninterrupted, boundary 120. Each of the boundaries 120 encloses an opening 140. The members 110 are interconnected, wherein the connection of the members 110 is based on interlocking or fitting into one another of the boundaries 120 of adjacent members 110. The boundaries 120 of adjacent members 110 preferably engage with one another such that the connected members 110 are moveable with respect to one another to a limited extent. The expansion or unfolding of the medical product 100 can be facilitated by gripping or holding elements 160. For example, as shown in FIG. 2c, the gripping or holding elements 160 can have a spherical configuration. Advantageously, the gripping or holding elements 160 are located after expansion or unfolding of the product 100 at the corners of the expanded or unfolded product.

Moreover, the statements concerning the product according to the invention 100 shown in FIG. 2a apply mutatis mutandis.

FIG. 3 shows a further embodiment of a medical product according to the invention 100. The medical product 100 comprises a plurality of members 110 (partially shown) and a covering element 170.

The covering element 170 preferably has a plate-type configuration.

For example, the members 110 can—as shown—have a ring-shaped configuration. Each member 110 has a peripheral, preferably closed, i.e. uninterrupted, boundary 120. Each of the boundaries 120 encloses an opening 140. The members 110 are interconnected, wherein the connection of the members 110 is based on interlocking or fitting into one another of the boundaries 120 of adjacent members 110. Preferably, the boundaries 120 of adjacent members 110 engage with one another such that the connected members 110 are moveable with respect to one another to a limited extent.

A part of the members 110 is connected to the covering element 170.

The medical product according to FIG. 3 is suitable in particular for use in filling and closing a bone cavity. In this case, filing of the bone cavity can be carried out in a particularly advantageous manner by means of the members 110 or a structure composed of the members 110, while covering or closing of the bone cavity can be carried out by means of the covering element 170.

FIG. 4 shows a further embodiment of a medical product according to the invention 100. The medical product 100 comprises a plurality of members 110 (partially shown) and an enclosing element 180.

The enclosing element 180 comprises a rectangular enclosing part 182 and two non-equilaterally triangular, in particular two right-angled triangular, enclosing parts 184: 186. Each of the triangular enclosing parts 184:186 is connected via its shorter cathetus to an opposite narrow side of the rectangular enclosing part 182. The free corners 185:187 of the enclosing parts 184; 186 point in the same direction respectively. The free corners 185:187 are formed respectively by the hypotenuse and the longer cathetus of the enclosing elements 184:186. The enclosing elements 184: 186 are further preferably arranged parallel or essentially parallel to each other. Moreover, the free corners 185:187 are preferably connected via a strut 188. In this way, the mechanical stability of the enclosing element 180 and thus the medical product 100 overall can be increased.

The enclosing elements 182:184:186 preferably have a plate-type configuration.

For example, the members 110—as shown—can have a ring-shaped configuration. Each member 110 has a peripheral and preferably closed, i.e. uninterrupted, boundary 120. Each of the boundaries 120 encloses an opening 140. The members 110 are interconnected, wherein the connection of the members 110 is based on interlocking or fitting into one another of the boundaries 120 of adjacent members 110.

Preferably, the boundaries 120 of adjacent members 110 fit into one another such that the connected members 110 are moveable with respect to one another to a limited extent.

One part of the members 110 is connected to an inner surface of the enclosing element 180.

Within the meaning of the present invention, the term "inner surface of the enclosing element" is to be understood to refer to the surface of the enclosing element that directly faces an area enclosed by the enclosing element. In other words, the inner surface of the enclosing element is the surface that immediately surrounds an area enclosed by the enclosing element.

In the product 100 shown in FIG. 4, a part of the members 110 can be connected for example to the inner surface 181 of the rectangular enclosing part 182 and/or the inner surface 183 of the triangular enclosing part 184 and/or the inner surface 189 of the triangular enclosing part 186. The figure shows securing of the members 110 on the inner surface 181 of the enclosing part 182 and the inner surface 183 of the enclosing part 184.

The medical product according to FIG. 4 is suitable in particular for use in a total hip arthroplasty.

Figure 5A:
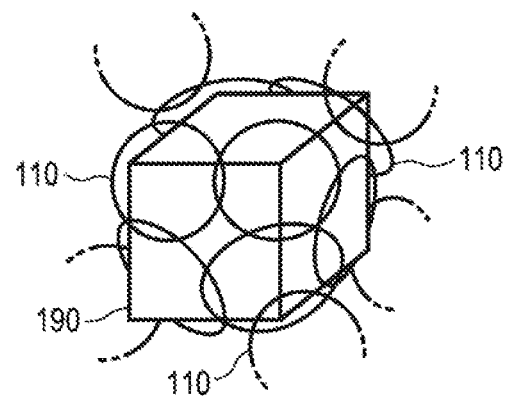
FIGS. 5a-c: further embodiments of a product according to the invention.

FIG. 5a partially shows a further embodiment of a medical product 100. The medical product 100 comprises a plurality of members 110 with a ring-shaped configuration. Each member 110 has a peripheral and preferably closed boundary. The members 110 are interconnected such that the boundaries of adjacent members 110 engage with one another, preferably such that the connected members 110 are moveable with respect to one another to a limited extent.

The medical product 100 further comprises additional structural elements that have a cubical configuration and are arranged or integrated inside the medical product 100, in particular in hollow spaces and/or interstices of the medical product 100.

FIG. 5a shows a partial view of such an additional structural element 190. The cubical structural element 190 is configured to be larger than the members 110. The cubical structural element 190 is arranged or integrated in a gap formed by interlocking members 110. Preferably, each corner of the cubical structural elements—as shown by the example of the structural element 190—extends through a member 110 having a ring-shaped configuration. In this manner, stabilizing/stiffening of the medical product can be achieved. At the same time, the unintentional release of the additional structural elements from the medical product 100 can be prevented.

Figure 5B:
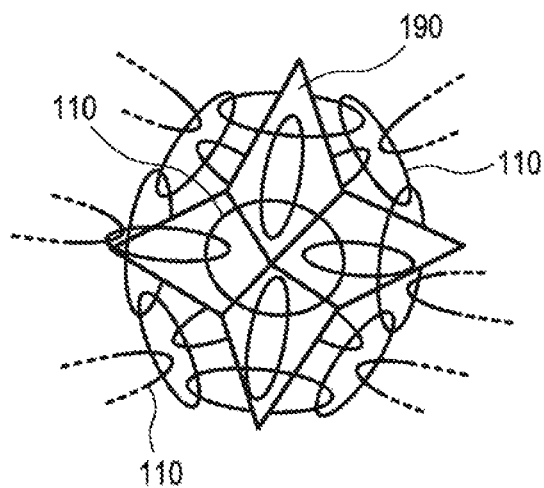

FIG. 5b shows a partial representation of a further embodiment of a medical product 100. The medical product 100 comprises a plurality of members 110 having a ring-shaped configuration and additional structural elements in the form of four pointed stars. The additional structural elements are arranged or integrated inside the medical product 100, in particular in hollow spaces and/or interstices of the medical product 100.

The partial representation of FIG. 5b shows such an additional structural element 190. The star-shaped structural element 190 is configured to be larger than the members 110. The star-shaped structural element 190 is arranged or integrated in a gap formed by interlocking members 110. Each point of the star-shaped structural elements—as shown in the example of the star-shaped structural element 190 preferably extends through a ring-shaped member 110. In this manner, stabilizing/stiffening of the medical product 100 can also be achieved without causing unintentional release of the additional structural elements from the medical product 100.

With respect to further features and advantages of the medical product 100, reference is made to the explanations of FIG. 5a.

Figure 5C:
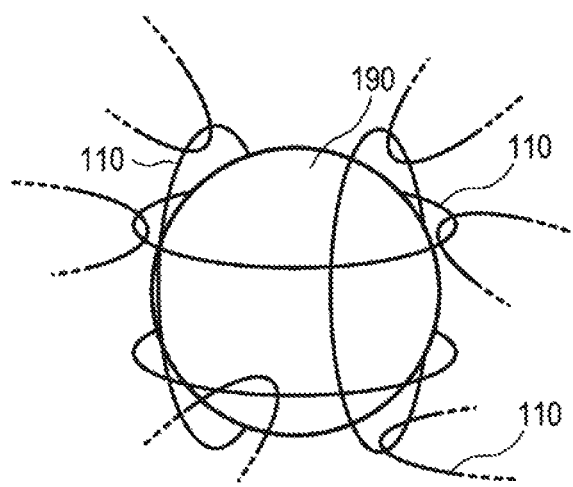

FIG. 5c shows a partial representation of a further embodiment of a medical product according to the invention 100. The medical product 100 comprises a plurality of members 110 having a ring-shaped configuration and additional structural elements in the form of spheres. The additional structural elements are arranged or integrated inside the medical product 100, in particular in hollow spaces and/or interstices of the medical product 100.

The partial representation of FIG. 5c shows such a structural element 190. The spherical structural element 190 is configured to be larger than the members 110. The spherical structural element 190 is arranged or integrated in a gap formed by interlocking members 110. Preferably, parts of the outer surface of the spherical structural elements—as shown in the example of the spherical structural element 190—extend respectively through a ring-shaped member 110. In this way, stabilizing/stiffening of the medical product 100 can also be achieved without the risk of unintentional release of the additional structural elements from the medical product 100.

With respect to further features and advantages of the medical product 100, reference is made to the explanations of FIG. 5a.

The embodiments shown in FIGS. 1 through 5 are preferably a surgical implant, and preferably a bone replacement material, in particular for lining bone or joint implants or for use as a counter-bearing for bone or joint implants.

EXEMPLARY EMBODIMENT

By means of CAD (computer-aided design), a medical product was designed in the form of a surgical implant that is suitable in particular for lining bone or joint implants or for use as a counter-bearing for bone or joint implants. The designed implant comprised a plurality of interconnected members with a ring-shaped configuration. In this case, the surgical implant was designed such that the boundaries of adjacent members engaged with one another or fitted into one another so that the connected members were moveable relative to one another to a limited extent.

The CAD data were then exported as an STL (STereo-Lithography standard tessellation language) file and imported into 3D printer software. The STL data were then processed in this software for printing. After this, the surgical implant was produced by 3D printing. After completion of production, the surgical implant was removed from the 3D printer, and any residues were cleaned off. Depending on the printing result, post-processing, in particular optimization and/or re-design of the CAT data and/or STL data, could be necessary in individual cases. The implant was then cleaned and subjected to quality assurance. After this, the surgical implant was packaged, and the package was labeled.

The process chain for producing a product according to the invention described above by way of example can of course comprise additional method steps. Depending on the intended function of the product, the production method can additionally comprise a coating step and optionally a subsequent cleaning step. Moreover, sterilization can be carried out before packaging the product. Finally, additional quality assurance can be carried out after packaging of the product and labelling of the package.

The invention claimed is:

1. A medical product for use in treating a bone cavity, wherein the product comprises a plurality of interconnected members, wherein each member has a peripheral boundary and the boundaries of adjacent members interlock, wherein the product comprises a three-dimensional structure composed of the members, wherein the three-dimensional structure further comprises a multilayer construction, wherein each layer has interconnected members, wherein the respective boundaries of members engage with adjacent layers, wherein the boundaries of adjacent members interlock in such a way that each of them engages with a through opening, a through hole, or a through channel of at least one adjacent member, wherein the medical product has additional structural elements in addition to the members, wherein the additional structural elements are located in hollow spaces and/or interstices of the medical product, and wherein the additional structural elements are configured to be larger than the members and wherein the additional structural elements are not connected to the members.

2. A medical product for use in treating a bone cavity, wherein the product comprises a plurality of interconnected members, wherein each member has a peripheral boundary and the boundaries of adjacent members interlock, wherein the product comprises a three-dimensional structure composed of the members, wherein the three-dimensional structure further comprises a multilayer construction, wherein each layer has interconnected members, wherein the respective boundaries of members engage with adjacent layers, wherein the boundaries of adjacent members interlock in such a way that each of them engages with a through opening, a through hole, or a through channel of at least one adjacent member, wherein the medical product has additional structural elements in addition to the members, wherein the additional structural elements are located in hollow spaces and/or interstices of the medical product, and wherein the additional structural elements are configured to be larger than the members, wherein the additional structural elements are configured to be larger than the hollow spaces and/or interstices of the medical product and wherein the additional structural members are not connected to the members.

3. The medical product of claim 2, wherein the hollow spaces and/or interstices are hollow spaces and/or interstices of a structure composed of the members.

4. The medical product of claim 2, wherein the additional structural elements have a polyhedral configuration.

5. The medical product of claim 4, wherein the polyhedral configuration is a cuboid, cubical, tetrahedral, prismatic, pyramidal, truncated pyramidal or spade-shaped configuration.

6. The medical product of claim 2, wherein the additional structural elements have a non-polyhedral configuration.

7. The medical product of claim 6, wherein the non-polyhedral configuration is a spherical, conical, truncated conical, ring-shaped, toroidal or circular-cylindrical configuration.

8. The medical product of claim 2, wherein the boundaries of the adjacent members engage with one another such that the connected members are moveable with respect to one another to a limited extent.

9. The medical product of claim 2, wherein each of a plurality of inner members of the plurality of interconnected members is connected to a plurality of further members of the plurality of interconnected members, and in that the product is externally bounded by a number of areas, each having interlocking members of the plurality of interconnected members along its surface.

10. The medical product of claim 2, wherein the structure can be unfolded into a polyhedral structure.

11. The medical product of claim 10, wherein the polyhedral structure is a cubical, cuboid, prismatic, pyramidal, spade-shaped structure or a structure delimited from free-form surfaces.

12. The medical product of claim 2, wherein the structure is a non-polyhedral structure.

13. The medical product of claim 12, wherein the non-polyhedral structure is a spherical, ellipsoid or conical structure.

14. The medical product of claim 2, wherein at least one part of the boundaries is closed.

15. The medical product of claim 2, wherein the members or the boundaries have a triangular, quadrangular, pentagonal, hexagonal, ellipsoid, ring-shaped, toroidal, cubical and/or star-shaped configuration or have a geometry or shape created from free-form surfaces.

16. The medical product of claim 2, wherein each of the members has an internal diameter of 0.1 mm to 20 mm.

17. The medical product of claim 2, wherein the members can be divided into two or more groups, wherein the members of each group are identically configured and the members of different groups are differently configured compared to the members of different groups.

18. The medical product of claim 17, wherein the members of different groups differ in at least one property that is selected from the group composed of total diameter, inner diameter, member size, member shape, member material, boundary width or thickness, color, additives and combinations of two or more of said properties.

19. The medical product of claim 2, wherein some members have a larger internal diameter than other members of the product.

20. The medical product of claim 2, wherein some members have a colored marking.

21. The medical product of claim 2, wherein members in rim, edge, and/or corner areas of the product have a colored marking.

22. The medical product of claim 2, wherein some members are interconnected such that they are not moveable relative to one another.

23. The medical product of claim 2, wherein the members comprise or are composed of a material that is selected from the group comprising metals, polymers, ceramic materials, bone cement materials and mixtures or combinations of two or more of said materials.

* * * * *